US008889404B2

(12) United States Patent
Rostalski et al.

(10) Patent No.: US 8,889,404 B2
(45) Date of Patent: Nov. 18, 2014

(54) METHOD AND APPARATUS FOR PRODUCING BIOGAS

(71) Applicant: KSB Aktiengesellschaft, Frankenthal (DE)

(72) Inventors: Kai Rostalski, Merseburg (DE); Peer Springer, Neuhofen (DE)

(73) Assignee: KSB Aktiengesellschaft, Frankenthal (DE)

( * ) Notice: Subject to any disclaimer, the term of this patent is extended or adjusted under 35 U.S.C. 154(b) by 0 days.

(21) Appl. No.: 13/632,502

(22) Filed: Oct. 1, 2012

(65) Prior Publication Data

US 2013/0029314 A1    Jan. 31, 2013

Related U.S. Application Data

(63) Continuation of application No. PCT/EP2011/054911, filed on Mar. 30, 2011.

(30) Foreign Application Priority Data

Apr. 1, 2010   (DE) .................. 10 2010 014 239

(51) Int. Cl.
| | |
|---|---|
| C12Q 3/00 | (2006.01) |
| C12M 1/36 | (2006.01) |
| C12M 1/107 | (2006.01) |
| C12M 1/34 | (2006.01) |
| C12M 1/06 | (2006.01) |

(52) U.S. Cl.
CPC ............ C12M 27/06 (2013.01); C12M 21/04 (2013.01); C12M 41/00 (2013.01); C12M 41/42 (2013.01); Y02E 50/343 (2013.01)
USPC ...... 435/286.5; 435/3; 435/286.7; 435/300.1; 210/739; 210/744; 210/702; 210/703

(58) Field of Classification Search
CPC ...... C12M 21/00; C12M 21/04; C12M 41/42; C12M 27/06; B01F 7/0025; B01F 7/00341; G01P 5/00; G01N 11/02
USPC ............. 435/300.1, 286.7, 3, 286.5; 210/739, 210/744, 702, 703
See application file for complete search history.

(56) References Cited

U.S. PATENT DOCUMENTS 5,476,573 A  *  12/1995  Hirose et al. ................... 202/197
6,508,881 B1    1/2003  Mueller et al.
(Continued)

FOREIGN PATENT DOCUMENTS

| CN | 1289043 A | 3/2001 |
|---|---|---|
| CN | 101671712 A | 3/2010 |

(Continued)

OTHER PUBLICATIONS

Machine Translation of EP 0474325 corresponding to DE 4028037 accessed Oct. 2013.*

(Continued)

*Primary Examiner* — William H Beisner
*Assistant Examiner* — Danielle Henkel
(74) *Attorney, Agent, or Firm* — Crowell & Moring LLP

(57) ABSTRACT

A method and apparatus for producing biogas from organic matter including a container (1) which is charged with fermentation substrate by a delivery system (13), and at least two stirring mechanisms (2) arranged in the container, the stirring mechanisms having propellers (3) which are rotated and generate mostly horizontal currents of the fermentation substrate in the container. The propeller diameters, the propeller geometries, and the positions of the propellers in the container are selected such that a shared mixing zone of the medium is generated in the container. Data for determining the mean speed and/or the viscosity of the medium in the mixing zone are detected and transmitted to a control unit (4) which varies actuating variables which modify the power input of the stirring mechanism into the mixing zone and/or the composition and/or the flow behavior of the container contents.

11 Claims, 3 Drawing Sheets

(56) References Cited

U.S. PATENT DOCUMENTS

| | | |
|---|---|---|
| 2011/0036779 A1* | 2/2011 | Bias et al. .................... 210/703 |
| 2012/0009664 A1 | 1/2012 | Buerger |

FOREIGN PATENT DOCUMENTS

| | | | | |
|---|---|---|---|---|
| DE | 31 26 552 A1 | | 1/1983 | |
| DE | 4028037 | * | 3/1992 | ............... C02F 3/28 |
| DE | 199 47 339 A1 | | 4/2001 | |
| DE | 20 2007 002 835 U1 | | 8/2007 | |
| DE | 102007063091 | * | 7/2009 | ............ C12M 1/107 |
| EP | 0 019 055 A1 | | 11/1980 | |
| EP | 1 086 827 A1 | | 3/2001 | |
| EP | 1 394 246 A1 | | 3/2004 | |
| EP | 1 762 607 A1 | | 3/2007 | |
| EP | 1 884 563 A1 | | 2/2008 | |
| WO | WO 83/00101 A1 | | 1/1983 | |
| WO | WO 2008/104320 A2 | | 9/2008 | |
| WO | WO 2009/071294 A2 | | 6/2009 | |

OTHER PUBLICATIONS

Machine Translation of DE102007063091 accessed Mar. 2013.*
International Search Report dated Jul. 8, 2011 with English translation (four (4) pages).
German Office Action dated Nov. 26, 2010(four (4) pages).
English-language translation of the International Preliminary Report on Patentability dated Oct. 11, 2012. (Six (6) pages).

* cited by examiner

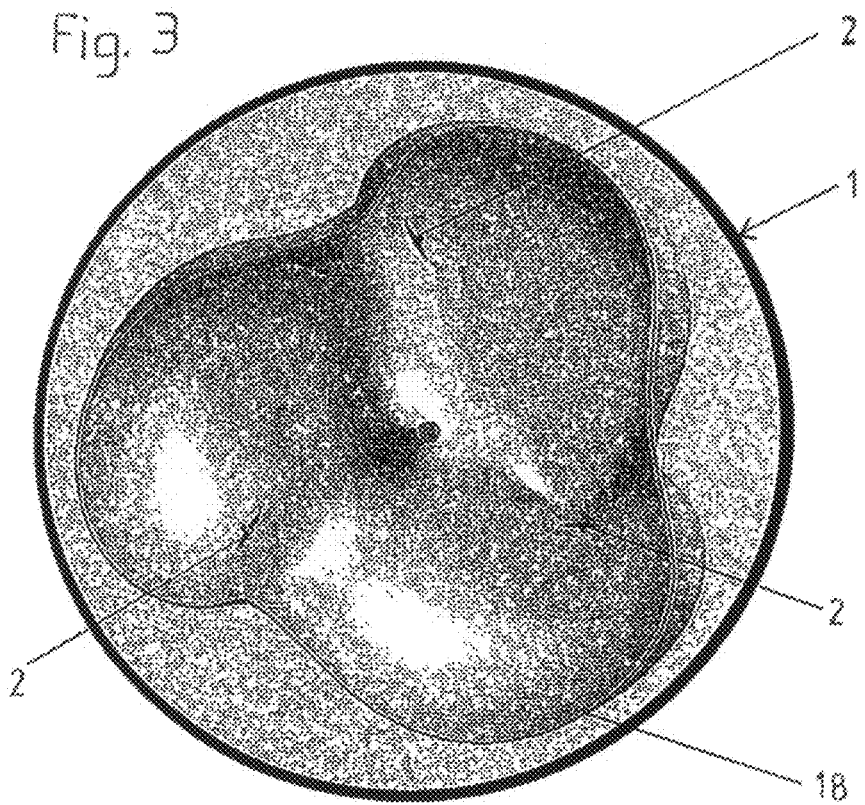

METHOD AND APPARATUS FOR PRODUCING BIOGAS

CROSS REFERENCE TO RELATED APPLICATIONS

This application is a continuation of international patent application no. PCT/EP2011/054911, filed Mar. 30, 2011 designating the United States of America and published in German on Oct. 6, 2011 as WO 2011/121024, the entire disclosure of which is incorporated herein by reference. Priority is claimed based on Federal Republic of Germany patent application no. DE 10 2012 014 239.5, filed Apr. 1, 2010, the entire disclosure of which is likewise incorporated herein by reference.

BACKGROUND OF THE INVENTION

The invention relates to a method and an apparatus for producing biogas from organic substances, substrate being supplied to a container by means of a feed system and there being arranged in the container at least two agitator mechanisms, the propellers of which are set in rotation via drives, the propellers generating in the container mostly horizontal flows of the container contents.

The method serves for generating biogas from organic substances. The raw substance used in such plants for generating biogas is designated as substrate. The substrate is composed of biologically degradable biomass, such as liquid manure, silage or biowaste. The containers used for the production of biogas are also designated as bioreactors or fermenters. When the biogas plants are being operated continuously, substrate is supplied continuously to the container and biogas and also fermentation residue are extracted. Substrate located in the container is converted by means of various types of microorganisms. This biomass to be converted is designated as fermentation substrate. Microbial breakdown gives rise from the fermentation substrate to methane and carbon dioxide as the main components of the biogas.

The substrate supplied is mixed with the container contents. The substrate is supplied mostly by punctiform feed with the aid of fodder systems. The biomass dwell time required for as high a biogas yield as possible is dependent critically upon the mixing of the substrate with the fermentation substrate. In the case of those media which are characterized predominantly by increased viscosities, circulation of the container contents is necessary for mixing and/or intermixing, this taking place, as a rule, by means of agitator mechanisms.

In the field of anaerobic bioreaction technology, fermenters with a height to diameter ratio greater than 0.5 are used in many applications. Mixing is in this case carried out mostly by means of vertical agitator mechanisms. The agitator mechanism propellers are in this case located on a central shaft driven from outside. The drive shaft is arranged vertically and projects into the container from above, while it mostly runs parallel to the container walls. Such a fermenter is known, for example, from German patent publication no. DE 199 47 339 A1.

Instead, the method according to the invention for producing biogas employs container forms, of which the height to diameter ratio is lower than 0.5. The diameter of the containers preferably lies between 16 and 40 meters. With these container dimensions, it is no longer economically viable to use a central vertical agitator mechanism driven from outside. For mixing the container contents, use is made of agitator mechanisms which are arranged predominantly in the marginal zone of the container and in the latter and which generate mostly horizontal flow of the medium in the container. Such an arrangement is known, for example, from US patent publication no. US 2012/0009664 (=WO 2008/104320).

German utility model no. DE 20 2007 002 835 U1 discloses a plurality of agitator mechanisms for intermixing the container contents, two agitator mechanisms arranged one above the other being arranged opposite an individual agitator mechanism. For high fermentation process efficiency, as uniform a biomass distribution as possible in the fermenter liquid is considered necessary. In addition, a filling level measurement device is provided, by means of which the filling height in the container is detected and a corresponding filling level measurement signal is generated as a height actual-value signal. A filling level measurement signal is delivered to a control device which, when a lower filling height is detected, activates a height servomotor for the agitator mechanism designed as a submersible motor agitator, such that the latter is lowered and its agitating blades are thereby completely submerged even further.

The fermentation substrates used for generating biogas usually have structurally viscous flow properties. Structurally viscous means that the dynamic viscosity of the fermentation substrate decreases with an increase in shear rate. Viscosity is therefore not a value, but a function. For each induced shear rate, an associated viscosity is obtained. The viscosity in the container is consequently locally different. It depends on the shear rates present locally. The reason for this is the local velocities which influence the flow in the container.

Shear rates are generated by the movement of the propeller of an agitator mechanism. In the surroundings of the propeller, the local viscosity decreases in the case of structurally viscous fermentation substrates. With an increase in distance from the propeller, the shear rate is reduced and the viscosity rises correspondingly. The result of this is that the propeller predominantly sucks in fermentation substrate from near-propeller regions where the fermentation substrate has a low viscosity. This gives rise to near-propeller regions in which the substrate is transported at high velocities in a small volume only around the propeller itself. These near-propeller regions are designated as caverns. Where agitator mechanisms operate only locally in a cavern, optimal intermixing of the container contents does not take place because the generation of flow is restricted to these regions. Consequently, this leads to a reduction in the useful reactor volume in relation to the actual capacity of the bioreactor. As a result, less biogas and therefore also less useful methane are generated in the smaller useful reactor volume. The methane fraction or methane quantity has effects upon the economically efficient operation of a bioreactor.

SUMMARY OF THE INVENTION

The object of the invention is to maximize the converted fermentation substrate quantity and the dwell time required for this purpose and also to form a larger effective mixing zone. The further object is to make available a method in which a plurality of agitator mechanisms generate a mixing zone, the energy outlay required for this purpose being minimized and the methane yield which results from the mixing zone being optimized.

This object is achieved, according to the invention, in that the propeller diameter, the propeller geometry and the position of the propellers are selected such that a common mixing zone of the medium can be generated in the container, and in that measurement data for determining the average velocity and/or viscosity of the medium in the mixing zone are detected and the measurement data are passed on to a regulating unit, the regulating unit being capable of varying manipulated quantities which vary the introduction of power from the agitator mechanisms into the mixing zone and/or the composition of the container contents. The aim is to enlarge the reaction volume.

With the aid of the method, it is possible to allow optimal mixing of the container contents, while at the same time minimizing the introduction of energy necessary for this purpose. In this case, a first agitator mechanism generates an agitator mechanism jet. A second agitator mechanism is positioned such that it transports the jet of the first agitator mechanism further on and thus itself generates a jet. By the agitator mechanisms being deliberately positioned and being operated in coordination with one another, the mixing volume between the individual agitator mechanisms is enlarged. For this purpose, according to the invention, the operation of additional agitator mechanisms is also switched by the regulating unit or the regulating unit varies the quantity and/or composition of the substrate supplied and/or of a recirculate.

Further, the average velocity of the flow of the fermentation substrate in the mixing zone and/or the viscosity in the mixing zone are/is detected. It proves especially advantageous if the average velocity in the mixing zone is used as a measure for an optimal introduction of energy. With the aid of this quantity, in the method according to the invention, the process is optimized in energy terms. If the agitator mechanisms are operated with hydraulic powers which are too low, the average outlet velocity, present at an agitator mechanism, of the fermentation substrate in the mixing zone is too low. The result of this is that the mixing zone breaks down into ineffective individual zones. The average velocities rise again in these on account of the high local shear rates, this being uneconomic in energy terms. If the agitator mechanisms are operated with hydraulic powers which are too high, the average velocity in the mixing zone rises above the amount required to form them, with the result that either the introduction of energy and/or the methane yield from the biogas are/is influenced unfavorably. Between these unfavorable operating conditions, there is an optimal velocity which, according to the invention, is used as a controlled quantity for an optimal introduction of energy and turnover in the container.

The optimal velocity depends on many factors, for example the position of the agitator mechanisms and/or the composition of the fermentation substrate. Specific optimal velocity values thus arise for each application, and in these values a minimization of the energy content is achieved by an optimal introduction of power and thrust from the agitator mechanisms into a common mixing zone. The positioning of agitator mechanisms is configured such that the agitator mechanisms do not operate in a limited way locally, but correspondingly to one another.

There is a direct relation in structurally viscous media between velocity and viscosity. Thus, alternatively or additionally to the velocity, the viscosity may also be used, as a function of the shear rate, for the hydraulic power necessary for energy-optimized intermixing of the container contents. For this purpose, direct or indirect determination of the power of one or of a plurality of agitator mechanisms takes place on the basis of electrical or mechanical measurement data.

The relation between velocity and viscosity can be described according to the Ostwald-De-Waele formulation. Local viscosity depends on the locally present shear rate. The latter, in turn, is related to the local velocity:

$$\eta = k \cdot \gamma^{m-1} = k \cdot \left(\frac{dv}{ds}\right)^{m-1}$$

with $\eta$: dynamic viscosity,
$\gamma$: shear rage, $$\frac{dv}{ds}:$$

velocity gradient
k, m: free parameters.

After measurement data for determining the average velocity and/or the viscosity in the mixing zone have been detected, the measurement data are passed on to a regulating unit. The regulating unit used may be, for example, a stored-program control.

The regulating unit compares the measurement values with plant-specific desired values. These may be the velocity values or viscosity values in the mixing zone, at which a common mixing zone is maintained, along with a minimal introduction of power from the agitator mechanisms. Furthermore, the substrates used for methane generation, their quantities and compositions and also their dwell time in the fermenter are important. The operationally specific desired values depend, for example, on the size of the container, on the type of agitator mechanisms and on the arrangement of the agitator mechanisms in relation to one another. They are fixed for each application.

In an especially preferred version of the invention, the manipulated quantity used is the rotational speed of the agitator mechanisms. If the velocity or viscosity deviates from their optimal values in terms of the introduction of power or the methane gas yield and/or the methane gas content, the regulating unit varies the rotational speed of the agitator mechanisms. If the velocity is too high or the viscosity too low, the rotational speed is lowered. If the velocity is too low or the viscosity too high, the regulating unit increases the rotational speed.

The introduction of power by the agitator mechanisms may also be varied in that further agitator mechanisms are cut in. The cut-in delivers an additional introduction of power and can thereby prevent the common mixing zone from breaking down into individual caverns.

The regulating unit can also vary manipulated quantities which vary the composition of the container contents. For this purpose, the regulating unit can increase or lower the quantity of substrates supplied. A further possibility is to vary the digestion of the fermentation substrate by the use of enzymes. Dilution of the fermentation substrate by means of liquid manure and/or recirculate and variation of the flow properties of the fermentation substrate by the addition of chemical or biological active mechanisms are also possible. In this case, even only a phased cut-in of one or more agitator mechanisms may take place, for example in the event of a temporary change in the substrate composition or the fermentation substrate composition by the routing of recirculate.

To determine the average velocity and the average viscosity in the mixing zone, various measurement methods may be employed. In an especially advantageous variant of the invention, the average velocity in the mixing zone is detected by ultrasonic probes. The advantage of this is that this is a contact-free measurement method. When the local velocities are being measured, the medium remains unaffected, since no additional obstruction is introduced into the flow. An additional obstruction would entail a change in the local shear rate. Contactless measurement methods are therefore preferably adopted.

Alternatively or additionally to velocity measurement, the flow behavior of the fermentation substrate may also be detected. In an especially advantageous variant of the method, the measurement data for determining the viscosity in the mixing zone are detected via the power consumption of the agitator mechanisms. For this purpose, preferably, a rotational speed-regulated agitator mechanism is employed. By a regulated variation in rotational speed for measurement purposes, the viscosity-dependent power coefficient can be determined as a function of the rotational speed and therefore of the shear rate in the agitator mechanism surroundings. The measurement of the viscosity occurring at the agitator mechanism is carried out by checking the power consumption of the agitator mechanism while the latter has a variable rotational speed. By comparison with a corresponding water curve, the medium viscosity dependent on shear stress can be determined. One aim is to detect the viscosity with the aid of evaluations so that the hydraulic power of one or more agitator mechanisms can be determined.

In a further version, measurement data for determining a floating layer and its thickness are detected during operation. These floating layers are formed when gas bubbles adhere to particles, and these rise and bond with the surface to form continuous layers. A layer of this kind may grow to an extent such that an outlet of gas from the fermentation substrate is no longer possible. The occurrence of these floating layers must therefore be prevented, and for this purpose at least one additional agitator mechanism is switched on which generates turbulence which dissolves the floating layer. The bonding of the particles to form a layer can be prevented by the turbulence, so that the particles can be stirred into the remaining fermentation substrate again.

In the method, preferably cylindrical containers are used for producing biogas. In this case, it proves especially beneficial if their ratio of height to diameter is lower than 0.5. Alternatively, ring containers or containers with peripheral flow can also be used.

BRIEF DESCRIPTION OF THE DRAWINGS

The invention will be described in further detail hereinafter with reference to illustrative preferred embodiments depicted in the accompanying drawing figures in which:

FIG. 3 shows a simulation of a flow generated in a container by means of three main agitator mechanisms.

DETAILED DESCRIPTION OF EMBODIMENTS

Figure 1:
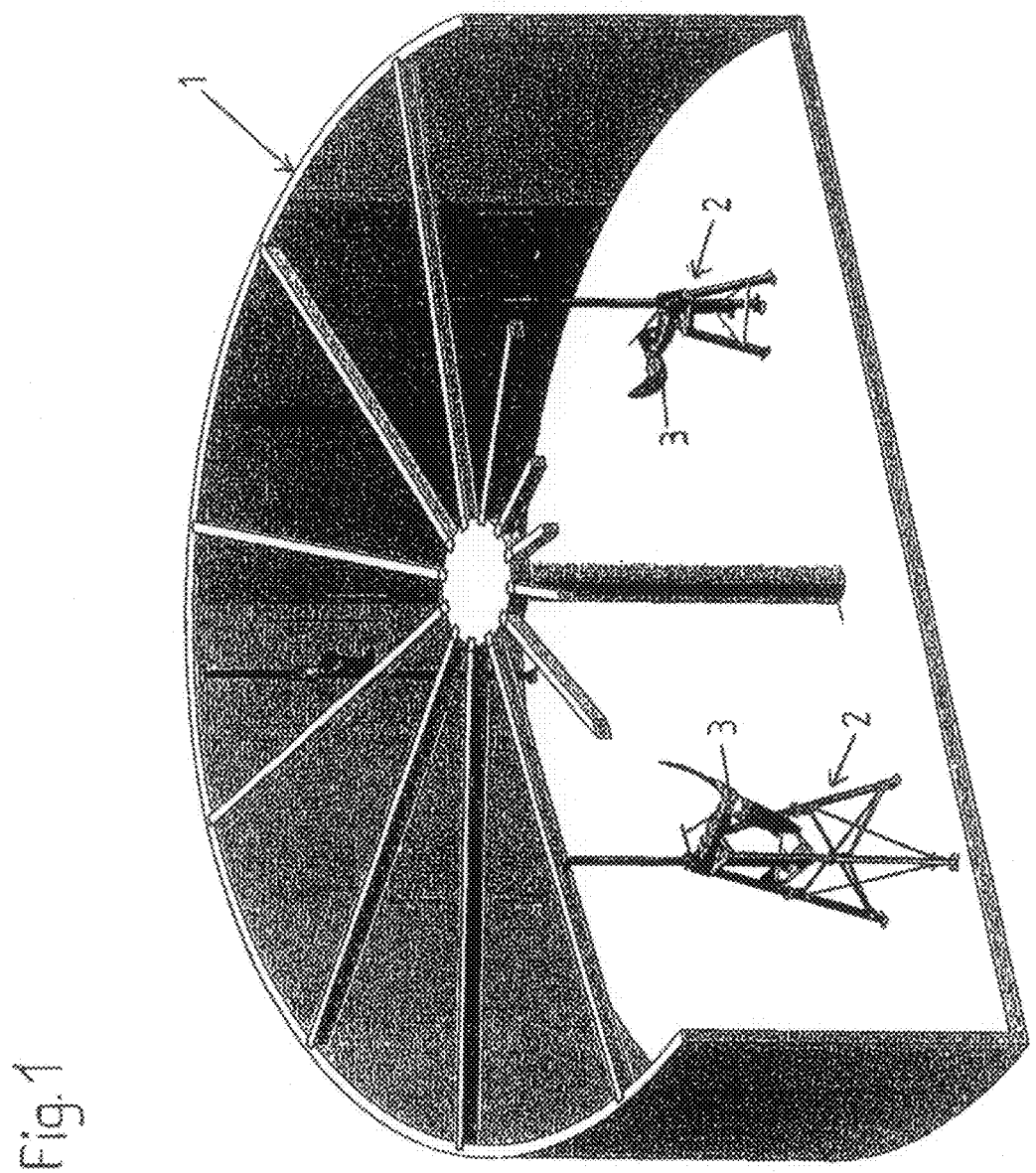
FIG. 1 is a perspective view of a container for biogas production with two main agitator mechanisms.

FIG. 1 illustrates a cylindrical container 1 for producing biogas. Other container forms are likewise possible. The ratio of the largest diameter to the height of the container is lower than 0.5. Positioned in the container 1 are two agitator mechanisms 2, the propellers 3 of which generate mostly horizontal flows of the fermentation substrate in the container 1. The agitator mechanisms 2 or their propellers 3 are arranged at different heights inside the container 1. An additional agitator mechanism 11 is cut in, as required.

Figure 2:
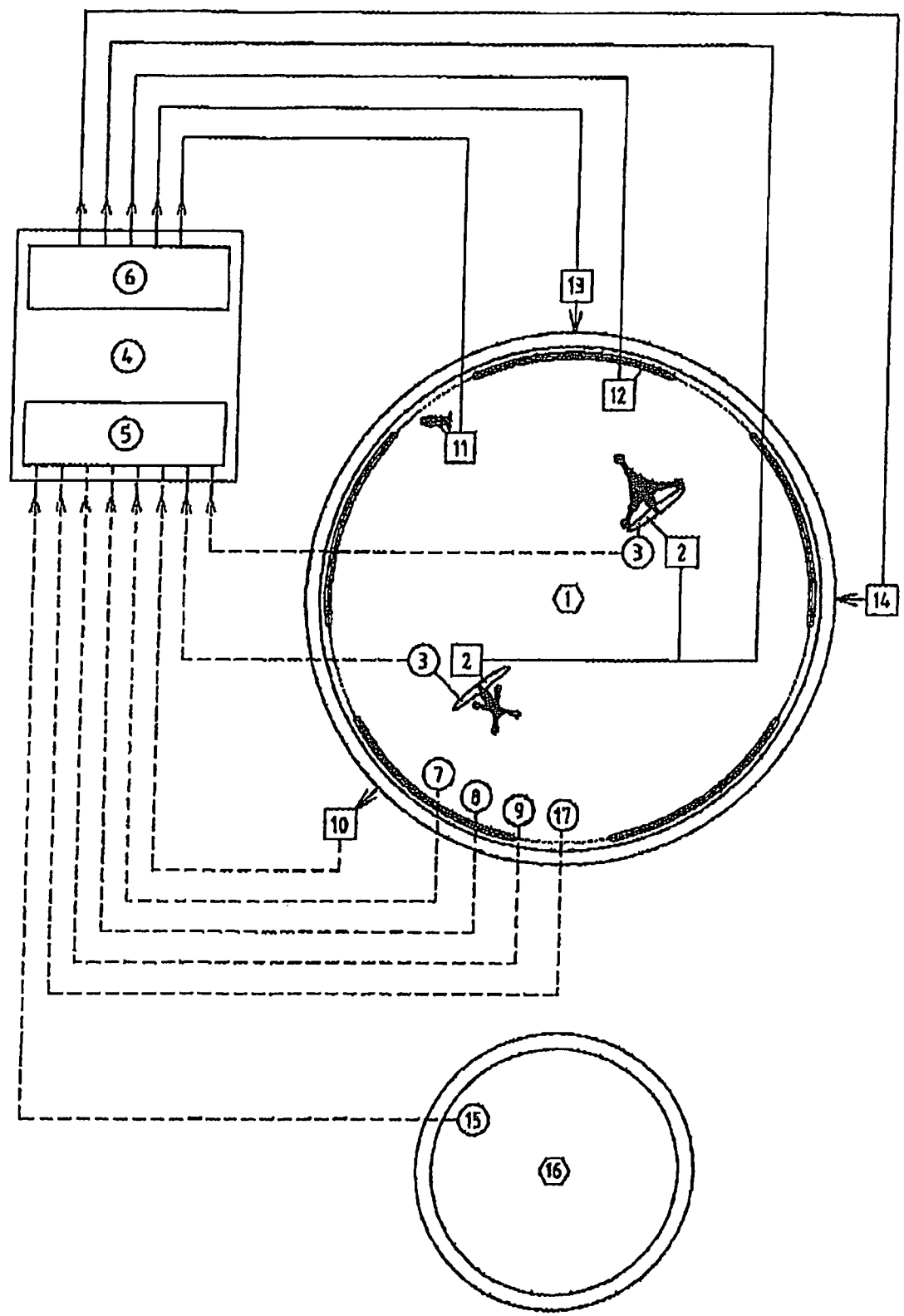
FIG. 2 is a diagrammatic illustration of the regulation of biogas production.

FIG. 2 shows a diagrammatically illustrated regulating unit 4 for a method for producing biogas. This may be a stored-program control (SPS) or another regulating system.

The regulating unit 4 has a signal input region 5 and a signal output region 6. The signals of the data which are detected during measurements of the method are conducted to the signal input region 5. Data from various process-monitoring sensors 7, 8, 9, 10, 15, 17 and from the agitator mechanisms 2 are processed in the regulating unit 4. The signal output region 6 is operatively connected to process-influencing assemblies. Process-influencing assemblies are the agitator mechanisms 2, 11, a fermenter heating unit 12, a feed system 13 and a recirculation unit 14. These are controlled such that individual process parameters can be optimized with the aim of a maximum methane yield.

The following sensors may be used for process monitoring: at least one sensor for viscosity measurement 7, one or more sensors for flow velocity measurement 8, at least one floating layer detector 9, a gas quantity meter 10, a unit 15 for fermentation residue analysis and at least one unit 17 for determining the flow behavior of the fermentation substrate.

The economic efficiency of a biogas plant is dependent essentially upon the specific energy consumption of the agitator technology or of the plant. This is dependent, inter alia, on the flow behavior of the fermentation substrate. One of the main aims, therefore, is to expend as low a hydraulic power as possible for operating purposes.

The sensor 7 serves to detect the viscosity. To determine the viscosity, measurement data which are determined via the agitator mechanisms 2 may also be used. Alternatively or additionally, it is possible to employ a separate flow behavior determination unit 17. Flow behavior determination may in this case take place individually or simultaneously at a plurality of locations. The determination of the flow behavior is necessary in order to avoid too critical a flow behavior in the container 1 in terms of relevant process parameters and also damage to all the agitator mechanisms 2, 11 used in the process and to optimize their specific energy consumption. The velocity generated in the fermentation substrate is of major importance in optimizing between the gas yield and the specific energy consumption.

The sensor 8 is used for velocity measurement in the container 1. In this case, the velocity can take place at different locations by means of one or more velocity determinations.

The formation of a floating layer is monitored by means of a detector 9. Since a floating layer top has an adverse effect upon the emission of biogas from the fermentation substrate, its occurrence must be avoided or it must be destroyed as soon as possible after it has occurred. For this purpose, for example, an additional agitator mechanism 11 can be cut in and/or the rotational speed of one or more main agitator mechanisms 2 can be varied. This gives rise to flow turbulence which dissolves the floating layer.

In a biogas plant, the generation of methane is a principle aim, and therefore, in the method, the generated gas mass flow and/or methane mass flow are/is detected via a gas mass meter 10. If the methane mass falls below a specific level, the regulating unit 4 adapts the process-influencing assemblies to the process conditions. The aim of fermentation is to utilize as large an amount of the biogas potential of the substrate as possible.

The fermentation residues are collected in a fermentation residue store 16. The determination of the biogas residue potential in the fermentation residue is carried out by means of the unit 15 and is a further possible input quantity for the regulating unit 4 and for the regulation of the agitator mechanisms 2, 11. Determination of the biogas residue potential may take place at various locations in the plant. If a specific biogas residue potential is overshot in the fermentation residue, the regulating unit 4 adapts the process-influencing assemblies 2, 11, 12, 13, 14 to the process conditions.

Basically, all the data from the signal input region 5 are processed in the regulating unit 4. The processing of the data takes place on the basis of a stored algorithm. This algorithm assumes the task of determining from the input quantities the values for controlled quantities determined from them. The controlled quantities determined are used to regulate the process-influencing assemblies 2, 11, 12, 13, 14 from the signal output region 6.

Signals for regulating various manipulated quantities emanate from the signal output region 6. Consequently, for example, agitator mechanisms 2 are activated, and their rotational speed can be regulated as a function of the average velocity in the mixing volume and/or of the viscosity in the mixing volume. If a specific limit velocity of the fermentation substrate is overshot or undershot, this may have an adverse affect upon flow formation and therefore upon the process. Furthermore, in the absence of movement on the surface of the fermentation substrate, a floating layer may be formed. Moreover, the absence of movement may cause the substrate or fermentation substrate to be fed in to be distributed only insufficiently in the container 1.

When new substrate is supplied or if a floating layer has occurred, an additional agitator mechanism 11 can be cut in or regulated. The heating unit 12 supplies heat to the container 1 when new substrate is being fed in. The substrate is supplied by the feed system 13. The fodder quantity can consequently be adapted to the process parameters. Overfodder of the container 1 with substrate would have an adverse effect upon the flow behavior in the container 1 and therefore on methane production. If the flow behavior changes adversely, the fodder quantity is reduced and/or other controlled quantities, such as, for example, the velocity or recirculate quantity, is/are varied.

If fodder quantities are too low, insufficient substrate is available for methane formation. With the aid of the gas mass meter 10 and/or an analysis of the biogas residue potential in the fermentation residue, this state is detected and foddering with substrate is induced. The method has a recirculation unit 14 which, for example, adds recirculate in a metered manner in the case of too critical a flow behavior. The aim is to vary the flow behavior of the fermentation substrate in order to allow flow correspondence between the agitator mechanisms 2. This correspondence of the agitator mechanisms ensures as optimal a reaction volume of the fermentation substrate as possible. Furthermore, an improvement in the flow behavior ensures better transport of the shear rate, with the result that a fermentation substrate cavern formed by the agitator mechanism jet becomes larger. What is optimal is for such caverns to flow one into the other, as is shown as a large cavern in FIG. 3. This ensures an improved gas output. As a result, the biogas and methane yields are improved. An improvement in the flow behavior is also possible by adding in a metered manner enzymes, trace elements or other substances modifying the flow behavior. A higher substrate turnover and an increased biogas yield are thereby achieved.

FIG. 3 illustrates a simulation of a flow generated in a container 1 by means of three horizontally arranged agitator mechanisms 2. Each agitator mechanism 2 generates a flow path. The distances of the agitator mechanisms 2 from one another are selected such that a common mixing zone of the fermentation substrate is generated in the container 1. The agitator mechanisms 2 are positioned such that the flow generated in each case by the adjacent agitator mechanism 2 is transported further on and therefore a common mixing zone is obtained. The limits of the mixing zone are fixed by velocity limit values. This velocity limit is illustrated at the surface by an unbroken line 18.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method for producing biogas from organic substances, wherein fermentation substrate is supplied to a container by a feed system; at least two agitator mechanisms are arranged in the container; said agitator mechanisms each have propellers which are rotated via drives and generate mostly horizontal flows of the fermentation substrate in the container; and said propellers each have a propeller diameter, a propeller geometry and a propeller position selected such that a common mixing zone of the fermentation substrate is generated in the container;

said method comprising:

measuring floating layer data indicating the presence or absence of a floating layer on the surface of the fermentation substrate in the container;

transmitting measured fermentation substrate velocity and/or viscosity data and the floating layer data to a regulating unit for adjusting the introduction of power from the agitator mechanisms into the mixing zone and at least one of the composition of the fermentation substrate and the flow behavior of the container contents; and adjusting said introduction of power from the agitator mechanisms into the mixing zone and at least one of the composition of the fermentation substrate and the flow behavior of the container contents as needed in response to the measured fermentation substrate velocity and/or viscosity data and/or floating layer formation data in order to maintain the fermentation substrate velocity and/or viscosity within target ranges without floating layer formation, wherein when the floating layer data indicates the presence of the floating layer the power introduced to the at least two agitator mechanisms is increased relative to the power introduced to the at least two agitator mechanisms when the floating layer is absent.

2. The method as claimed in claim 1, wherein the regulating unit varies the rotational speed of at least one of the agitator mechanisms.

3. The method as claimed in claim 1, wherein the regulating unit activates or deactivates at least one additional agitator mechanism.

4. The method as claimed in claim 1, wherein the regulating unit varies:

the quantity and/or composition of the supplied fermentation substrate; or the quantity and/or composition of a recirculated stream of fermentation substrate; or the flow characteristics of the fermentation substrate.

5. The method as claimed in claim 1, wherein the average velocity in the mixing zone is detected by an ultrasonic probe.

6. The method as claimed in claim 1, wherein measurement data for determining the fermentation substrate viscosity or flow behavior are detected via the power consumption of one or more agitator mechanisms.

7. The method as claimed in claim 1, wherein power consumption of one or more agitator mechanisms is determined directly or indirectly from electrical or mechanical measurement data.

8. The method as claimed in claim 1, wherein measurement data for determining the viscosity of the fermentation substrate are detected by a viscosimeter.

9. The method as claimed in claim 1, wherein measurement data for determining a thickness of the floating layer is detected.

10. The method as claimed as claimed in claim 9, wherein at least one additional agitator mechanism is activated when the floating layer occurs, said at least one additional agitator mechanism generating turbulence which dissolves the floating layer.

11. The method as claimed in claim 1, wherein said container has a ratio of height to largest diameter less than 0.5.

* * * * *